(12) United States Patent
Edgar, Jr. et al.

(10) Patent No.: US 6,393,311 B1
(45) Date of Patent: May 21, 2002

(54) METHOD, APPARATUS AND SYSTEM FOR REMOVING MOTION ARTIFACTS FROM MEASUREMENTS OF BODILY PARAMETERS

(75) Inventors: Reuben W. Edgar, Jr.; August J. Allo, Jr., both of San Antonio, TX (US); Jesus D. Martin, Wallingford, CT (US); John R. DelFavero, East Hampton, CT (US); Michael B. Jaffe, Cheshire, CT (US)

(73) Assignee: NTC Technology Inc., Wilmington, DE (US)

( * ) Notice: Subject to any disclaimer, the term of this patent is extended or adjusted under 35 U.S.C. 154(b) by 0 days.

(21) Appl. No.: 09/410,991

(22) Filed: Oct. 1, 1999

Related U.S. Application Data

(60) Provisional application No. 60/104,422, filed on Oct. 15, 1998.

(51) Int. Cl.[7] .................................................. A61B 5/00
(52) U.S. Cl. ...................... 600/323; 600/336; 600/310; 600/324
(58) Field of Search ................. 600/309–311, 322–326, 600/330–331, 336, 473, 476; 356/39–41; 369/60.01

(56) References Cited

U.S. PATENT DOCUMENTS

| | | | | |
|---|---|---|---|---|
| 4,800,495 A | * | 1/1989 | Smith .......................... | 600/322 |
| 4,942,877 A | * | 7/1990 | Sakai et al. .................. | 600/323 |
| 4,955,379 A | * | 9/1990 | Hall ............................ | 600/366 |
| 5,025,791 A | | 6/1991 | Niwa | |
| 5,190,038 A | | 3/1993 | Polson et al. | |
| 5,266,417 A | | 7/1993 | Swedlow et al. | |
| 5,299,120 A | * | 3/1994 | Kaestle ....................... | 600/310 |
| 5,349,952 A | * | 9/1994 | McCarthy et al. .......... | 600/473 |
| 5,351,685 A | | 10/1994 | Potratz | |
| 5,368,026 A | | 11/1994 | Swedlow et al. | |
| 5,368,224 A | | 11/1994 | Richardson et al. | |
| 5,398,680 A | | 3/1995 | Polson et al. | |

(List continued on next page.)

OTHER PUBLICATIONS

Dowla, et al., Neural Networks and Wavelet Analysis in the Computer Interpretation of Pulse Oximetry Data, Neural Networks for Signal Processing VI—Proc. IEEE, 1996 IEEE Signal Process, Soc., IEEE Workshop, 0–7803–3550–3 (1996).

*Primary Examiner*—Eric F. Winakur
*Assistant Examiner*—Matthew Kremer
(74) *Attorney, Agent, or Firm*—TraskBritt

(57) ABSTRACT

A method for removing motion artifacts from devices for sensing bodily parameters and apparatus and system for effecting same. The method includes analyzing segments of measured data representing bodily parameters and possibly noise from motion artifacts. Each segment of measured data may correspond to a single light signal transmitted and detected after transmission or reflection through bodily tissue. Each data segment is frequency analyzed to determine dominant frequency components. The frequency component which represents at least one bodily parameter of interest is selected for further processing. The segment of data is subdivided into subsegments, each subsegment representing one heartbeat. The subsegments are used to calculate a modified average pulse as a candidate output pulse. The candidate output pulse is analyzed to determine whether it is a valid bodily parameter and, if yes, it is output for use in calculating the at least one bodily parameter of interest without any substantial noise degradation. The above method may be applied to red and infrared pulse oximetry signals prior to calculating pulsatile blood oxygen concentration. Apparatus and systems disclosed incorporate methods disclosed according to the invention.

34 Claims, 11 Drawing Sheets

U.S. PATENT DOCUMENTS

| | | |
|---|---|---|
| 5,431,170 A | 7/1995 | Matthews |
| 5,448,991 A | 9/1995 | Polson et al. |
| 5,482,036 A | 1/1996 | Diab et al. |
| 5,490,505 A | 2/1996 | Diab et al. |
| 5,555,882 A | 9/1996 | Richardson et al. |
| 5,588,427 A | 12/1996 | Tien |
| 5,632,272 A | 5/1997 | Diab et al. |
| 5,645,060 A | 7/1997 | Yorkey |
| 5,685,299 A | 11/1997 | Diab et al. |
| 5,713,355 A | 2/1998 | Richardson et al. |
| 5,743,263 A | 4/1998 | Baker, Jr. |
| 5,769,785 A | 6/1998 | Diab et al. |
| 5,800,348 A | 9/1998 | Kaestle |
| 5,803,910 A | 9/1998 | Potratz |
| 5,820,550 A | 10/1998 | Polson et al. |
| 5,852,638 A * | 12/1998 | Chen et al. .................. 375/344 |
| 5,853,364 A | 12/1998 | Baker, Jr. et al. |
| 5,885,213 A | 3/1999 | Richardson et al. |
| 5,919,134 A | 7/1999 | Diab |
| 5,934,277 A | 8/1999 | Mortz |
| 6,067,462 A * | 5/2000 | Diab et al. .................. 600/310 |
| 6,098,038 A * | 9/2000 | Hermansky et al. ......... 704/226 |
| 6,122,535 A * | 9/2000 | Kaestle et al. ............... 600/322 |

* cited by examiner

METHOD, APPARATUS AND SYSTEM FOR REMOVING MOTION ARTIFACTS FROM MEASUREMENTS OF BODILY PARAMETERS

CROSS-REFERENCE TO RELATED APPLICATION

This utility patent application claims the benefit of U.S. provisional patent application Ser. No. 60/104,422, filed Oct. 15, 1998.

BACKGROUND OF THE INVENTION

1. Technical Field

This invention relates to the field of signal processing. More particularly, this invention relates to processing measured signals to remove unwanted signal components caused by noise and especially noise caused by motion artifacts.

2. State of the Art

The measurement of physiological signals can often be difficult because the underlying physiological processes may generate very low level signals. Furthermore, interfering noise is inherent in the body and the interface between the body and sensors of physiological processes, Examples of physiological measurements include: measurement of electrocardiogram (ECG) signals based on the electrical depolarization of the heart muscle, blood pressure, blood oxygen saturation, partial pressure of $CO_2$, heart rate, respiration rate, and depth of anesthesia. ECG signals, for example, are typically detected by surface electrodes mounted on the chest of a patient. ECG signals are weak at the signal source (i.e., the heart) and are even weaker at the surface of the chest. Furthermore, electrical interference from the activity of other muscles (e.g., noise caused by patient breathing, general movement, etc.) causes additional interference with physiological signals such as an ECG. Thus, considerable care must be taken in the design and use of physiological processors to enhance the quality of the true signal and reduce the effects of interfering noise signals.

It is convenient to characterize a measured signal as being a composite signal composed of a true signal component and a noise signal component. The terms "measured signal" and "composite signal" will be used interchangeably hereinafter. Signal processors are frequently used to remove noise signal components from a composite measured signal in order to obtain a signal which closely, if not identically, represents the true signal. Conventional filtering techniques such as low pass, band pass, and high pass filtering can be used to remove noise signal components from the measured composite signal where the noise signal component occupies a frequency range outside the true signal component. More sophisticated techniques for conventional noise filtering include multiple notch filters, which are suitable for use where the noise signal component exists at multiple, distinct frequencies, all outside the true signal frequency band.

However, it is often the case that the frequency spectrum of the true and noise signal components overlap and that the statistical properties of both signal components change with time. More importantly, there are many cases where little is known about the noise signal component. In such cases, conventional filtering techniques are ineffective in extracting the true signal.

The measurement of oxygen saturation in the blood of a patient is a common physiological measurement the accuracy of which may be compromised by the presence of noise. Knowledge of blood oxygen saturation can be critical during surgery. There are means of obtaining blood oxygen saturation by invasive techniques, such as extracting and testing blood removed from a patient using a co-oximeter. But, such invasive means are typically time consuming, expensive, and uncomfortable for the patient. Fortunately, non-invasive measurements of blood oxygen saturation can be made using known properties of energy attenuation as a selected form of energy passes through a bodily medium. Such non-invasive measurements are performed routinely with a pulse oximeter.

The basic idea behind such energy attenuation measurements is as follows. Radiant energy is directed toward a bodily medium, where the medium is derived from or contained within a patient, and the amplitude of the energy transmitted through or reflected from the medium is then measured. The amount of attenuation of the incident energy caused by the medium is strongly dependent on the thickness and composition of the medium through which the energy must pass, as well as the specific form of energy selected. Information about a physiological system can be derived from data taken from the attenuated signal of the incident energy transmitted or reflected. However, the accuracy of such information is reduced where the measured signal includes noise. Furthermore, non-invasive measurements often do not afford the opportunity to selectively observe the interference causing the noise signal component, making it difficult to remove.

A pulse oximeter is one example of a physiological monitoring system which is based upon the measurement of energy attenuated by biological tissues and substances. More specifically, a pulse oximeter measures the variable absorption caused by arterial blood volume changes. Pulse oximeters transmit electromagnetic energy at two different wavelengths, typically at 660 nm (red) and 940 nm (infrared, hereinafter IR) into the tissue and measure the attenuation of the energy as a function of time. The output signal of a pulse oximeter is sensitive to the pulsatile portion of the arterial blood flow and contains a component which is a waveform representative of the patient's arterial pulse. This type of signal, which contains a component related to the patient's pulse, is called a plethysmographic waveform or plethysmogram.

Pulse oximetry measurements typically use a digit, such as a finger, or an ear lobe or other element of the body, where blood flows close to the skin as the medium through which light energy is transmitted. The finger, for example, is composed of various tissues and substances including skin, fat, bone, muscle, blood, etc. The extent to which each of these biological tissues and substances attenuate incident electromagnetic energy is generally known. However, the effect of motion can cause changes in the optical coupling of the sensor (or probe) to the finger, the underlying physiology, the local vasculature, optical properties of tissues due to changing optical path length as well as combinations and interactions of the all of the above. Thus, patient motion may cause erratic energy attenuation.

A typical pulse oximeter includes a sensor, cabling from the sensor to a computer for signal processing and visual display, the computer and visual display typically being included in a patient monitor. The sensor typically includes two light emitting diodes (LEDs) placed across a finger tip and a photodetector on the side opposite the LEDs. Each LED emits a light signal at different frequencies. The detector measures both transmitted light signals once they have passed through the finger. The signals are routed to a computer for analysis and. display of the various parameters measured.

The underlying physical basis of a pulse oximeter is Beer's law (also referred to as Beer-Lambert's or Bouguer's law) which described attenuation of monochromatic light traveling through a uniform medium which absorbs light with the equation:

$$I_{transmitted} = I_{incident} e^{-dc\alpha(\lambda)}, \quad (1)$$

where $I_{transmitted}$ is the intensity of the light transmitted through the uniform medium, $I_{incident}$ is the intensity of incident light, d is the distance light is transmitted through the uniform medium, c is the concentration of the absorbing substance in the uniform medium, expressed in units of mmol $L^{-1}$, and $\alpha(\lambda)$ is the extinction or absorption coefficient of the absorbing substance at wavelength $\lambda$, expressed in units of L/(mmol cm). The properties of Beer's law are valid even if more than one substance absorbs light in the medium. Each light absorbing substance contributes its part to the total absorbance.

Each LED emits light at different wavelengths, typically red (centered at about 660 nm) and IR (centered at about 940 nm) frequency bands. The intensity of light transmitted through tissue, $I_{transmitted}$, is different for each wavelength of light emitted by the LEDs. Oxyhemoglobin (oxygenated blood) tends to absorb IR light, whereas deoxyhemoglobin (deoxygenated blood) tends to absorb red light. Thus, the absorption of IR light relative to the red light increases with oxyhemoglobin. The ratio of the absorption coefficients can be used to determine the oxygen saturation of the blood.

To estimate blood oxygen saturation, $SpO_2$, a two-solute concentration is assumed. A measure of functional blood oxygen saturation level, $SpO_2$, can be defined as:

$$SpO_2 = \frac{c_o}{c_r + c_o}, \quad (2)$$

where $c_o$ represents oxyhemoglobin solute concentration, and $C_r$ represents reduced or deoxyhemoglobin solute concentration.

Noise signal components in a measured pulse oximetry light signal can originate from both AC and DC sources. DC noise signal components may be caused by transmission of electromagnetic energy through tissues of relatively constant thickness within the body, e.g., bone, muscle, skin, blood, etc. Such DC noise signal components may be easily removed with conventional filtering techniques. AC noise signal components may occur when tissues being measured are perturbed and, thus, change in thickness while a measurement is being made. Such AC noise signal components are difficult to remove with conventional filtering techniques. Since most materials in and derived from the body are easily compressed, the thickness of such matter changes if the patient moves during a non-invasive physiological measurement. Thus, patient movement can cause the properties of energy attenuation to vary erratically. The erratic or unpredictable nature of motion artifacts induced by noise signal components is a major obstacle in removing them.

Various approaches to removing motion artifacts from measured physiological signals, and particularly for use in pulse oximeters, have been proposed. U.S. Pat. Nos. 5,482, 036, 5,490,505, 5,632,272, 5,685,299, and 5,769,785, all to Diab et al., and U.S. Pat. No. 5,919,134 to Diab, disclose methods and apparatuses for removing motion artifacts using adaptive noise cancellation techniques. The basic proposition behind the Diab et al. approach is to first generate a noise reference signal from the two measured signals, and then use the noise reference signal as an input to an adaptive noise canceler along with either or both of the measured signals to remove the reference noise signal from the measured signals, thus approximating the actual parametric signals of interest. The Diab et al. approach appears to require the use of both measured input signals to generate a noise reference signal.

Another approach to noise artifact elimination is disclosed in U.S. Pat. No. 5,588,427 to Tien. Tien uses fractal dimension analysis to determine the complexity of waveforms in order to determine the proper value of the ratio of true intensities based on signal complexity. The Tien approach employs a fractal analyzer to determine values for two ratios, $\alpha$ and $\beta$, based on the measured time varying intensity of the transmitted red and IR light signals including noise. $\alpha$ is defined as the ratio of the time varying true intensity of light transmitted from the red LED and the time varying true intensity of the light transmitted from the IR LED. $\eta$ is a similar ratio relating the noise introduced during the measurement of the light transmitted by the red LED and the noise introduced during the measurement of the light transmitted by the IR LED. According to Tien, a fractal analyzer then determines values for $\alpha$ and $\beta$ and provides ($\alpha,\beta$) pairs to a statistical analyzer. The statistical analyzer performs analysis of one or more ($\alpha,\beta$) pairs to determine the best value for $\alpha$, which is then provided to a look-up table. The look-up table provides a value corresponding to the arterial oxygen saturation in the patient. While the Tien approach appears to be an innovative use of fractal analysis, it also appears to be computationally complex.

Yet another approach to noise artifact elimination is disclosed in U.S. Pat. Nos. 5,885,213, 5,713,355, 5,555,882 and 5,368,224, all to Richardson et al. The basic proposition behind the Richardson et al. approach is to switch operative frequencies periodically based on evaluating the noise level associated with various possible frequencies of operation in order to select the frequency of operation that has the lowest associated noise level. It would appear that data measured at a noisy frequency, using the Richardson et al. approach may be invalid or useless for calculating arterial oxygen saturation. Furthermore, Richardson et al. requires a computational overhead to constantly monitor which frequency of operation provides the least noise.

Another approach to noise artifact elimination is disclosed in U.S. Pat. No. 5,853,364 to Baker, Jr et al. The Baker, Jr. et al. approach first calculates the heart rate of the patient using an adaptive comb filter, power spectrum and pattern matching. Once the heart rate is determined, the oximetty data is adaptively comb filtered so that only energy at integer multiples of the heart rate are processed. The comb filtered data and the raw oximetry data are filtered using a K nan filter to adaptively modify averaging weights and averaging times to attenuate motion artifact noise. The adaptive filtering of the Baker, Jr. et al. approach appears to add significant computational complexity to solve the problem of motion artifact rejection.

Still another approach to noise artifact elimination is disclosed in U.S. Pat. No. 5,431,170 to Mathews. Mathews couples a conventional pulse oximeter light transmitter and receiver with a transducer responsive to movement or vibration of the body. The transducer provides an electrical signal varying according to the body movements or vibrations, which is relatively independent of the blood or other fluid flow pulsations. Mathews then provides means for comparing the light signals measured with the transducer output and performing adaptive noise cancellation. An apparent disadvantage of the Mathews approach is the need for a secondary sensor to detect motion.

Thus, a need in the art exists for a method, apparatus and system to eliminate motion-induced noise artifacts from light signals, that is relatively simple computationally, and that does not require more than one sensor.

SUMMARY OF THE INVENTION

The present invention includes methods, apparatuses and systems for removing noise in physiological measurements caused by motion or other similar artifacts. The methods, apparatuses and systems of the present invention eliminate noise from light signals using a single conventional sensor and are relatively simple computationally.

In a method embodiment, a segment of data from a measured pulse oximetry signal is conventionally filtered, and frequency analyzed for major frequency components. The frequency components with the largest power spectral density are selected for subdividing into subsegments, each comprising an individual heartbeat. The subsegments are averaged and then analyzed to determine if the averaged subsegment is a valid pulse oximetry signal. Additionally, various quality or confidence measures may be used to evaluate the validity of such signal. Valid averaged subsegments become outputs for further processing to calculate physiological parameters such as blood oxygen saturation levels.

A circuit card embodiment includes a processor and memory for storing a computer program capable of executing instructions embodying the above method.

A system embodiment includes an input device, an output device, a memory device and a motion artifact rejection circuit card capable of executing instructions stored in the memory device implementing the methods described herein.

Finally, a system embodiment includes an input device, and output device, a memory device and a processor, which may be a digital signal processor, capable of executing instructions stored in the memory device implementing the methods described herein.

BRIEF DESCRIPTION OF THE DRAWING FIGURES

In the drawings, which illustrate what is currently regarded as the best mode for carrying out the invention and in which like reference numerals refer to like parts in different views or embodiments:

DETAILED DESCRIPTION OF THE INVENTION

The following detailed description discloses methods, apparatuses and systems for removing motion artifacts from measured plethysmographic waveforms, particularly, but without limitation, those used in pulse oximetry. A system embodiment of the invention includes pulse oximetry hardware and associated software to perform the motion artifact suppression. A method embodiment of this invention includes a series of steps which exploits certain characteristics of plethysmographic waveforms. The methods, apparatuses and systems described below are suitable for light transmitted or reflected through bodily tissues and substances. For convenience, the following detailed description will assume measurement of light which has been transmitted through a finger of a human. The terms "signal" and "waveform" are used interchangeably herein.

Figure 1:
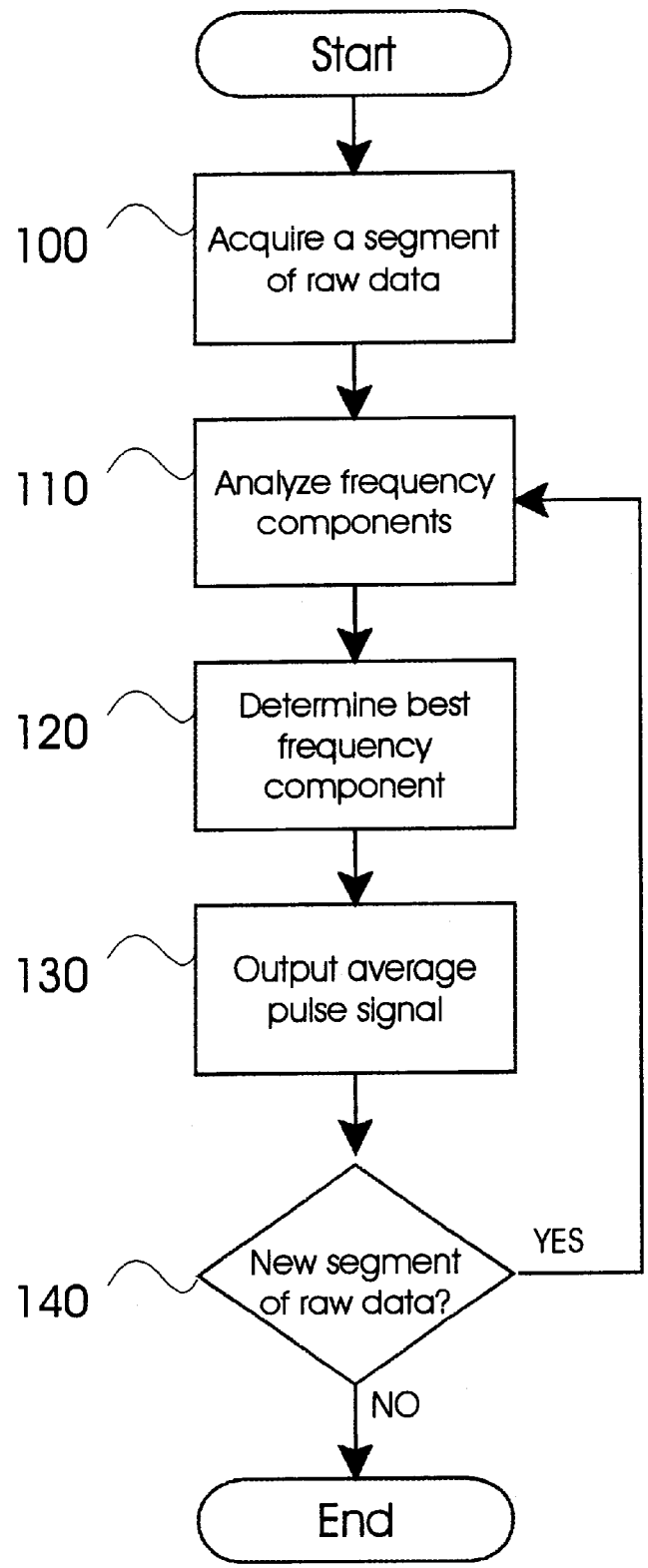
FIG. 1 is a high-level flowchart of a method embodiment of the invention.

FIG. 1 is a high-level flowchart of a method embodiment of the invention. The method steps include acquiring a segment of raw data 100, either red or IR, analyzing the data segment for dominant frequency components 110, determining the frequency component which represents a valid plethysmographic pulse 120, computing an average pulse based on the correct frequency component 130 and repeating for new raw data segments 140. In order to calculate blood oxygen concentration, $SpO_2$, the method embodiment of the invention may be applied to both red and IR data signals to eliminate or reduce noise from the data signals prior to calculating $SpO_2$.

Figure 2:
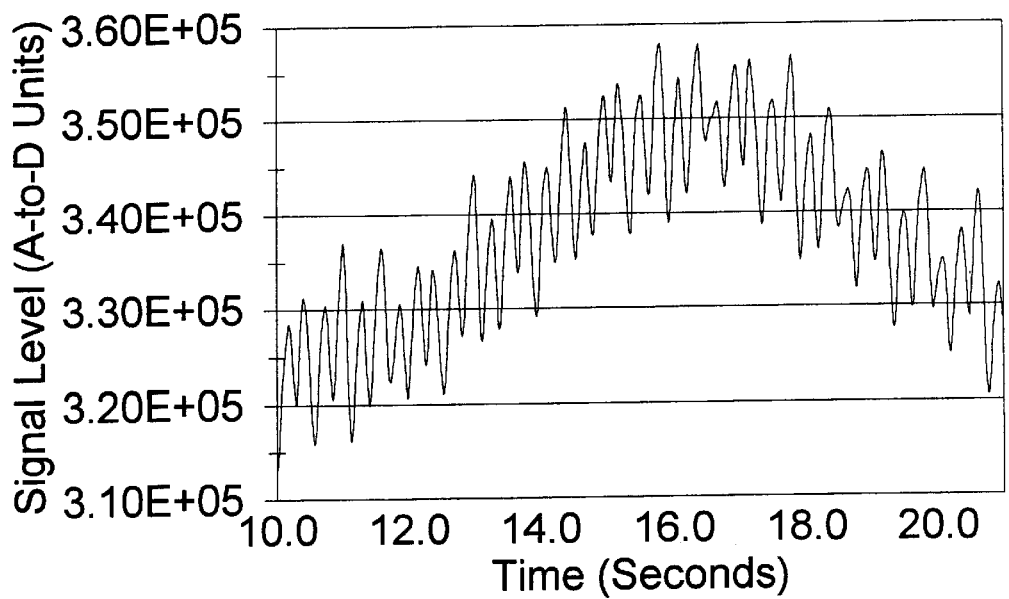
FIG. 2 is a graph of a segment of data representing transmitted infrared (IR) light data signal received by a pulse oximetry sensor suitable for signal processing in accordance with the invention.

The method of this invention begins with acquiring a segment of data (e.g., five or more pulses or approximately ten seconds) measured from a single light source transmitted through a finger and detected with a sensor on the opposite side of the finger. Acquiring a data segment is illustrated by block 100 of FIG. 1. For convenience, a 10.24 second segment of data will be used to illustrate the method. This corresponds to 1024 data points with a sampling rate of 100 data points per second. It should be readily apparent that the method of the invention is not limited to data segments of this size. FIG. 2 is an example of such a data segment for an IR light source. The signal processing steps described herein may be performed on both red and IR data segments independently and simultaneously. Thus, while the steps of the method may be illustrated with data from an IR light signal, the same steps are applicable to data from a red light signal and vice versa. The terms "data segment", "input waveform", "data signal" and "signal" are used interchangeably herein.

Figure 3:
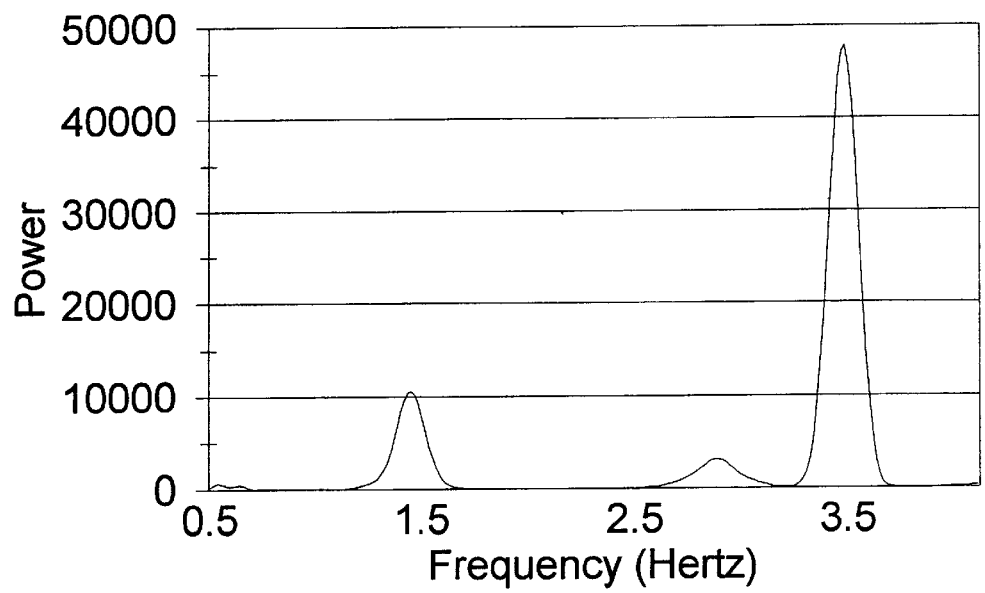
FIG. 3 is a graph of the power spectrum of the IR data segment in FIG. 2 in accordance with the invention.

A segment of data may be received from a sensor that converts transmitted or reflected light signals into electrical signals. Once a segment of data from a single electrical signal has been acquired, it may be filtered to reduce spectral leakage resulting from frequency analysis. There are several window filters which may be suitable for such purposes. For example, and not by way of limitation, a Hanning window may be used to reduce spectral leakage. It will be readily apparent to one of skill in the art of digital signal processing that other window filters and methods of filtering data to reduce spectral leakage may be selected for reducing spectral leakage. As methods of filtering and various filters are known to one of skill in the art of signal processing, they will not be further detailed herein. The filtered data is then frequency analyzed to determine the dominant frequency components, see block 110 of FIG. 1. FIG. 3 illustrates the power spectrum of the IR data segment of FIG. 2 after filtering.

Signal processing as described herein is generally performed in the frequency domain. The segment of data is converted into the frequency domain by, for example, performing the well-known Fast Fourier Transform (FFT) on the data. Other common techniques of converting time-domain data to the frequency domain may also be used, e.g., classical methods using the FFT such as the periodogram or correlogram, autoregressive methods, Prony's method, minimum variance methods, maximum likelihood methods. Additionally, time domain data may be converted to the frequency domain using transforms such as discrete cosine transform, wavelet transform, discrete Hartley transform, and Gabor transform.

Both transient and periodic noise artifacts can induce peaks in the frequency domain that may be larger than the peak caused by the patient's heart rate. The frequency peak which actually represents the patient's heart rate must then be determined, see block 120 of FIG. 1. One approach to determining the correct frequency is to order the frequencies by peak amplitude from largest to smallest, $F_1$ to $F_n$, where $F_1$ through $F_n$ are not harmonics of each other, and analyze them one by one to find the correct frequency, i.e., the patient's heart rate. For purposes of illustration, only the frequencies associated with the two largest power spectrum amplitude (peaks), $F_1$ and $F_2$, will be used to explain the signal processing in accordance with the invention. It will be readily apparent that the signal processing described herein may be extended from 2 to n candidate frequencies. For convenience of notation, $F_1$ is the frequency of the largest amplitude peak, and $F_2$ is the next largest peak, which is not a harmonic of $F_1$.

Where this is not the first analysis cycle, an additional check is made to determine if one of the two potential frequencies, $F_1$ and $F_2$, is similar to a known valid frequency, $F_0$, of the patient's heart rate as determined during the previous analysis cycle. Otherwise, the signal processing proceeds as described in the next paragraph. Historical trends in heart rate may be used to select the proper frequency peak. In the case where none of the candidate frequencies is similar to the previous heart rate frequency, e.g., both frequencies $F_1$ and $F_2$ are large amplitude noise frequencies, the smaller amplitude frequency of the two potential frequencies is discarded, and the previous heart rate frequency is selected as the second potential frequency. Thus, the method of the invention prevents the situation where there is no correct frequency to choose because of multiple large amplitude noise frequencies.

Once candidate frequencies $F_1$ and $F_2$ have been selected, each is processed separately to determine which is more likely to be the frequency of the patient's heart rate. Analyzing $F_1$ first, the data segment may be optionally filtered with a narrow bandstop filter at (or near) $F_2$ to "notch out" that frequency's influence on the data. Alternatively, each candidate frequency is analyzed in turn without "filtering out" the effects of the other frequencies. The signal processing continues by determining the beginning and end of each heartbeat pulse within the data segment in order to subsegment the data into its consecutive heartbeat pulses.

The period of rhythmic contraction of the heart by which blood is driven through the aorta and pulmonary artery is known as systole. Maximum light absorbance occurs during the systole of a cardiac cycle and is indicated on a plethysmogram by a low point or systolic valley. Conversely, the period of rhythmic relaxation and dilation of the heart cavities occurs during diastole when blood is drawn into the heart cavities. Minimum light absorbance occurs during the diastole of a cardiac cycle and is indicated on a plethysmogram by a high point or diastolic peak. While it is theoretically possible to use a first derivative of the data segment to identify transitions between diastole and systole and vice versa, in practice, the data may be so noisy that the first derivative provides useless information.

Figure 4:
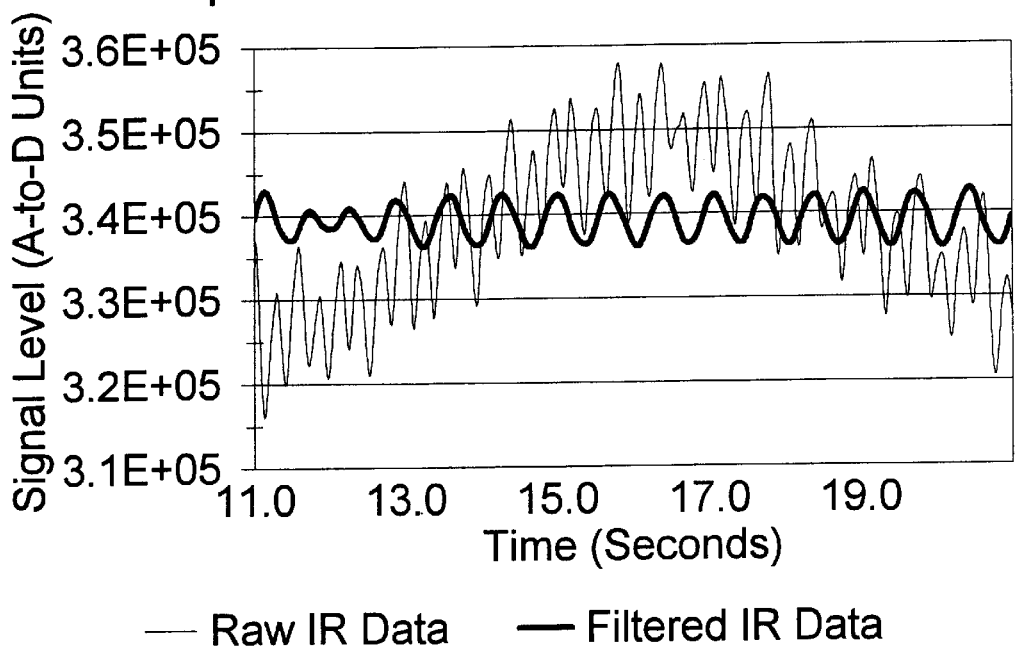
FIG. 4 illustrates a bandpass filtered IR data segment superimposed on the original IR data segment of FIG. 2 in accordance with the invention.
Figure 11:
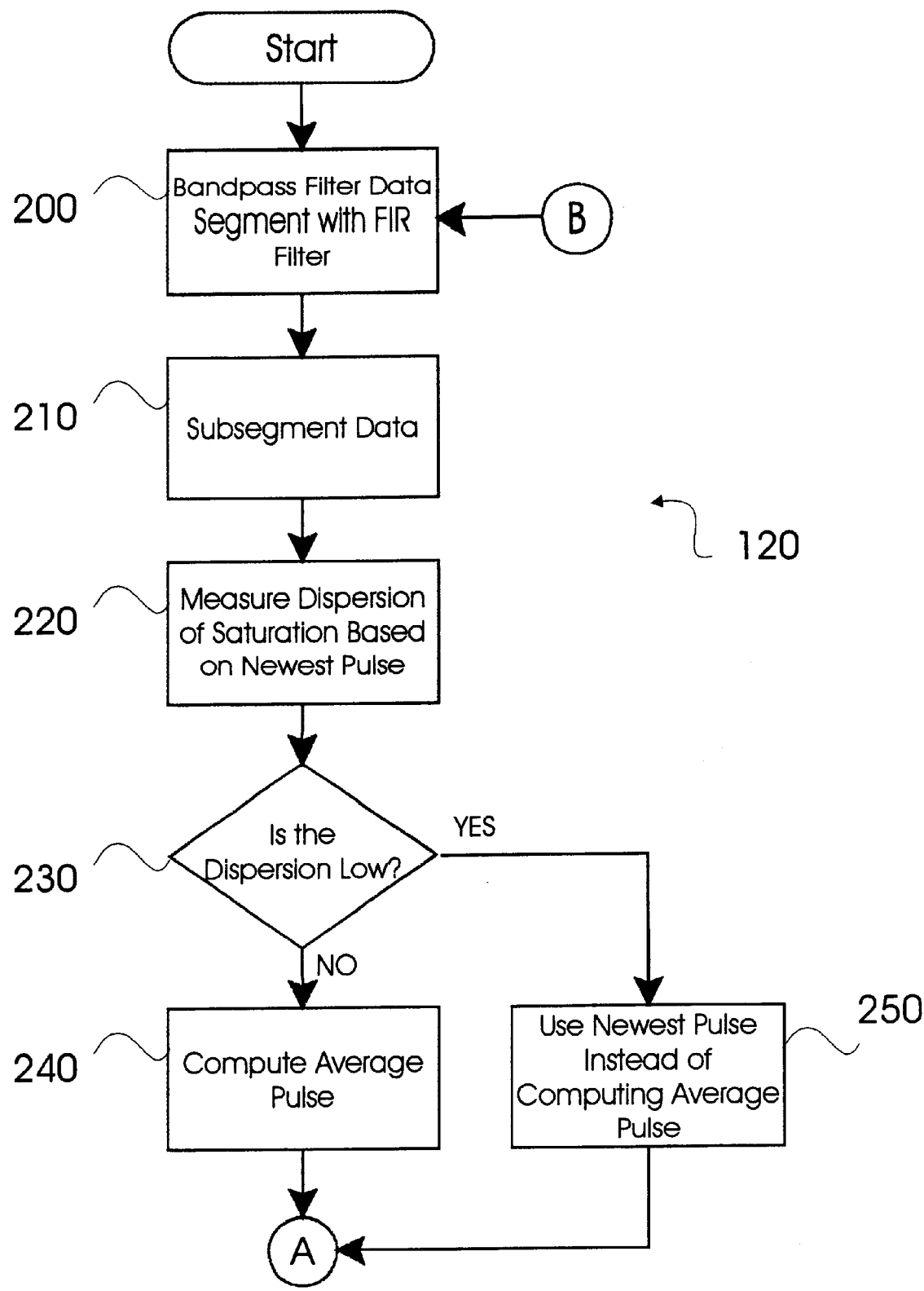
FIGS. 11 and 12 are a detailed flowchart of the method of determining the best frequency component, block 120, of FIG. 1.

Subsegmenting each pulse within a data segment according to the invention begins with a narrow bandpass filter at (or near) $F_1$ with a frequency spread (bandpass window width) of approximately ±0.25 Hertz about the center frequency of $F_1$, see block 200 of FIG. 11. To improve discrimination, especially with closely spaced peaks, the bandpass filter coefficients may be generated and adjusted as needed so that the center frequency is nearly identical to the candidate frequency, $F_1$. The resulting bandpass filtered data will resemble a sinusoidal waveform and is used to identify the point of diastolic peak for each pulse. Diastolic peaks in the data segment will occur at or near peaks in the sinusoidal waveform of the bandpass filtered data. FIG. 4 illustrates the bandpass filtered data superimposed on the original IR data segment of FIG. 2.

Each pulse subsegment is defined as starting one quarter pulse width before a diastolic peak and ending approximately one quarter pulse width after the next diastolic peak, see block 210 of FIG. 11. This ensures that each heartbeat pulse is centered within its pulse subsegment. The DC level or bias is determined by taking the mean of the data points in each subsegment. Each pulse subsegment may be detrended by subtracting the DC level, or pulse subsegment mean, from each data point in the pulse subsegment.

After subsegmenting the data segment into individual pulses, it is preferred to compute the dispersion of saturation values for the latest pulse, see block 220 of FIG. 11. Measures of the distribution or dispersion of the oxygen saturation values may be calculated using the individual data samples, or combinations thereof with a pulse or averaged pulse. The measure of dispersion may be used to determine whether there is sufficient noise in the data segment to warrant additional signal processing. For example, where the dispersion is very low, then the use of previous data in combination with the latest pulse would not be required, see blocks 230 and 250 of FIG. 11. Where the dispersion is higher, then the pulses for the time interval being evaluated may be combined to create an average pulse, see blocks 230 and 240 of FIG. 11. The individual pulse or average pulse may then be evaluated using a number of criteria or rules, see below. If the pulse under evaluation is found to be acceptable, the saturation could be calculated a number of ways including using the mean or mode of the dispersion of the data samples of the individual pulse or average pulse or at a particular time or phase of the pulse.

Figure 12:
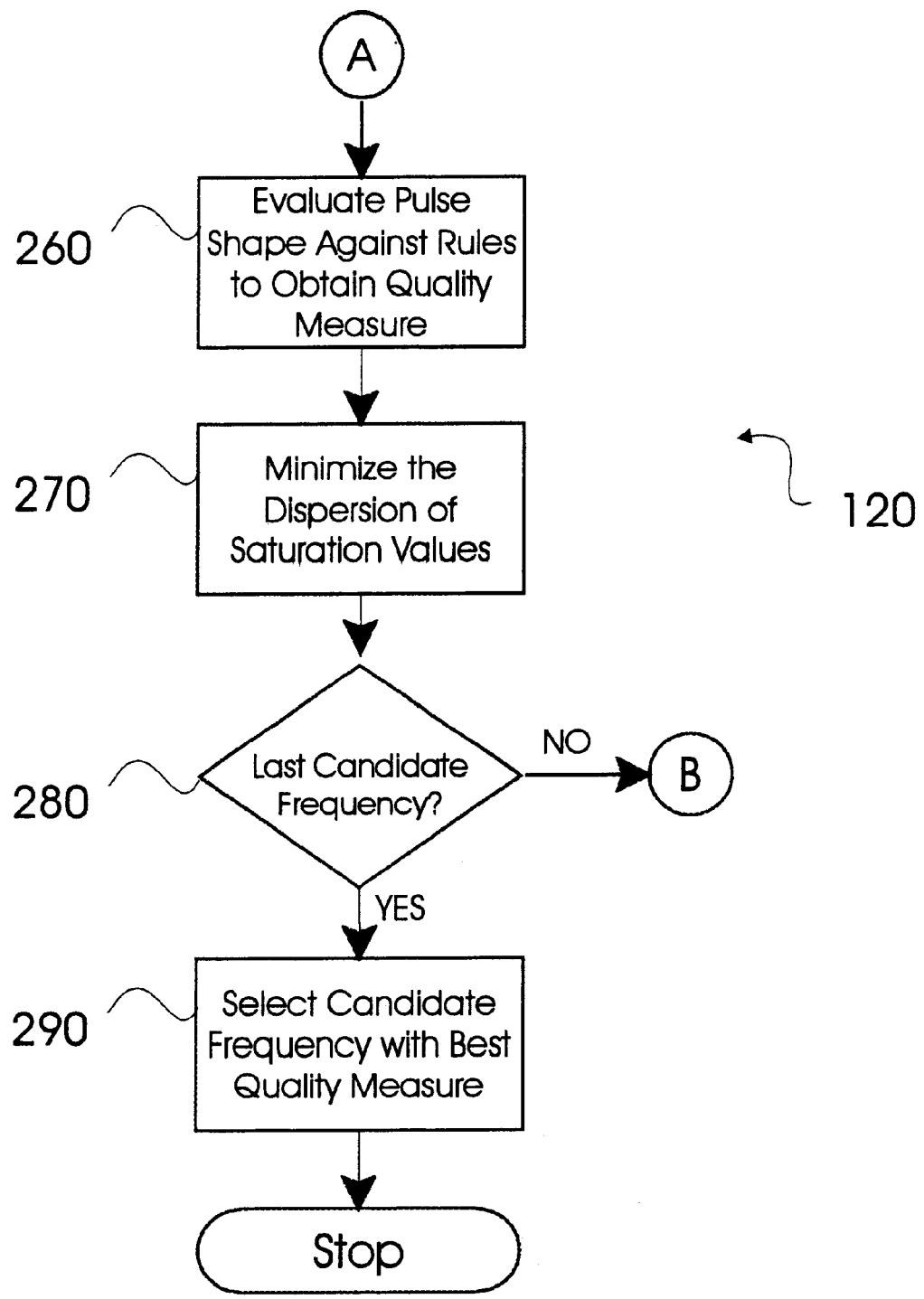

Additionally, it is important to minimize the dispersion of the saturation values because the red and IR signals operate on an alternating basis in the time domain, see block 270 of FIG. 12. The preferred embodiment minimizes the dispersion of the saturation values by adjusting the phase relationship of the red and IR signals. The phase relationship of the red and IR signals may be adjusted, for example and not by way of limitation, by changing the delay or filtering the signals. Additionally, the delay required to adjust the phase relationship of the red and IR signals, and thus, to minimize the dispersion of the saturation values, may be variable. It is believed that the variation in this delay may be due in part to system to system differences (e.g., monitor and/or sensor differences) and other factors (e.g., drive current changes due to physiological and anatomical specifics of the patient's measurement site). Because the optimum phase delay between the signals varies, it is desirable to adjust it on a beat to beat basis.

An exemplary method of minimizing dispersion of saturation values varies the delay over a range such as about ±20 ms in 1 ms steps from the nominal values. The range may be swept sequentially (i.e., from −20 ms to +20 ms) or may be performed optimally using analytical or empirical search techniques, for example, and not by way of limitation, by using the Simplex Method or any other suitable search technique. The delayed interpolated waveform may be estimated using linear interpolation or higher order interpolation methods. Methods of interpolation are known to one of skill in the art and will not be further detailed. At each step the saturation is calculated for each data sample in the individual or average pulse waveform. A histogram of saturation values is generated using bin sizes of 0.25 percent. A measure of the dispersion is then calculated.

The currently preferred measure of dispersion is to find the percentage of all saturation values calculated falling within the tallest bin and its two immediately surrounding bins. The delay is then adjusted and the process repeated until all steps of the range have been tested or a minimum dispersion found using an analytical or empirical search algorithm. Dispersion may be considered "very low" where at least 75% of the saturation values calculated fall within the largest (or tallest) bin and its immediately surrounding bins, i.e., 75% of the calculated saturation values fall in a saturation range of 0.75% (3 bin widths). The method of minimizing dispersion by locating an optimal delay as described above is exemplary only. Other methods of minimizing dispersion and locating an optimal delay will be readily apparent to one of skill in the art and should be considered within the spirit and scope of the invention.

Any suitable means for computing the "central tendency" of the subsegmented pulses or an "average pulse" may be used according to the invention, see block 240 of FIG. 11. Two modified mean averaging methods for computing an average pulse will be detailed below. Both averaging methods are modified by eliminating data points used for computing the average according to various statistical outlier tests. Any suitable statistical outlier test may be used according to the invention and those detailed below are exemplary only. The terms "average" and "mean" are used interchangeably throughout.

The first method for computing an average pulse includes storing the data subsegments in a two-dimensional (2-D) array in computer memory so that each row of the 2-D array represents a subsegment. A modified mean is applied to each of the columns of the 2-D array, respectively. The mean is modified by first determining the standard deviation of the equivalent points of the subsegments. The standard deviation will allow a statistical determination as to whether a point should be included in the calculation of the mean or excluded. The preferred embodiment of this statistical outlier test is more pessimistic about points at the beginning and end of the subsegments (±1 standard deviation) and less pessimistic about points at the middle of the subsegments (±3 standard deviations). The threshold profile for including data points so defined may be linear from beginning to middle and linear from middle to end. Alternatively, the threshold profile may have a smooth curvature with maximum at the middle of the subsegments. Once the 2-D array has been averaged using the modified mean technique, the DC level associated with the last subsegment is applied to the averaged subsegment (trended) in the case where the data was previously detrended.

Figure 5:
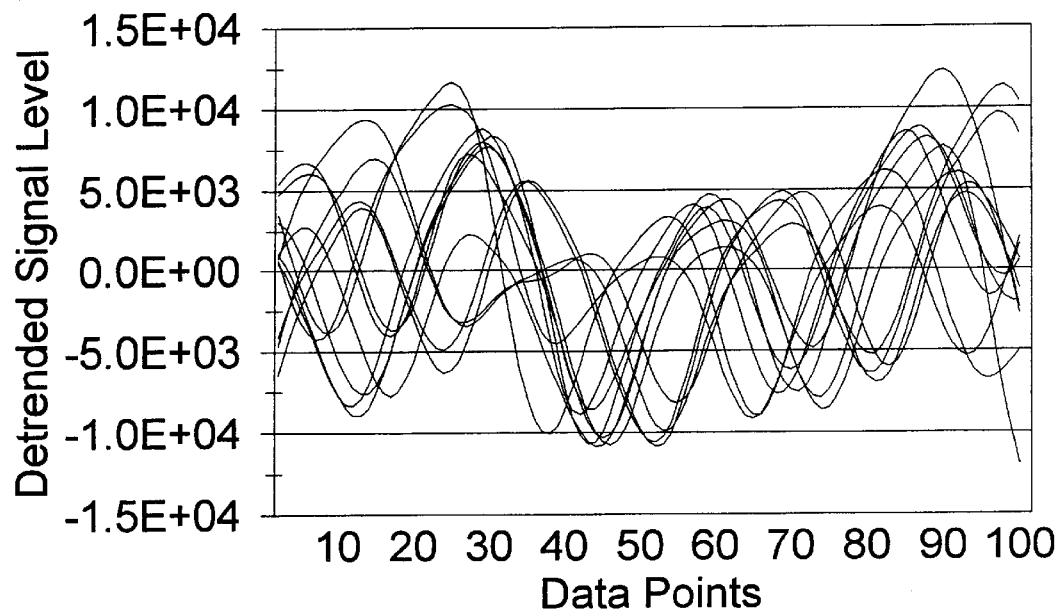
FIG. 5 is a graph of each pulse subsegment detrended and superimposed upon one another in accordance with the second method of computing an average pulse.
Figure 6:
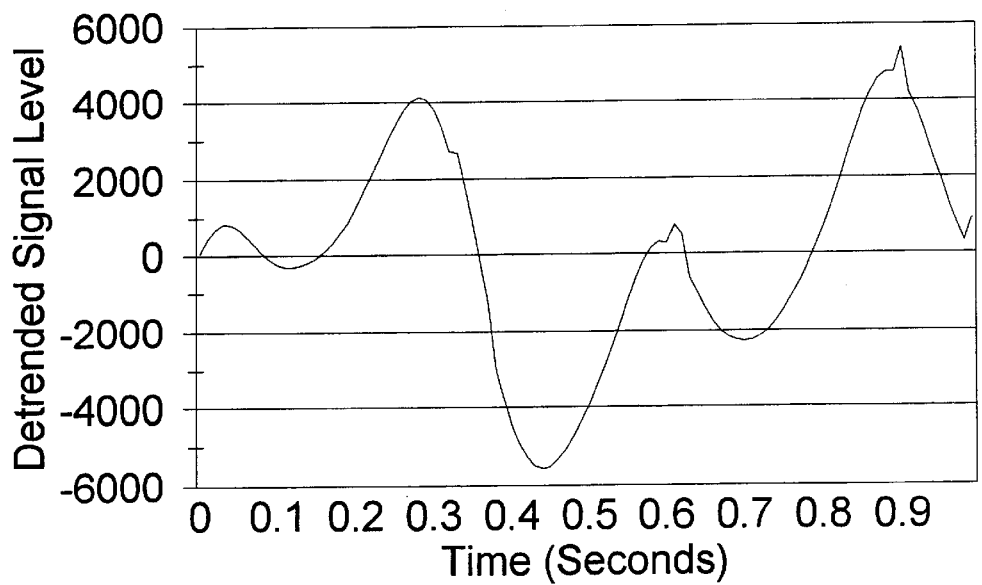
FIG. 6 shows the modified average pulse as computed from the detrended pulse subsegments shown in FIG. 5.

The second method for computing an average pulse includes calculating the mean and standard deviation of each pulse subsegment. Applying the statistical outlier of this second method, only data points within ±2 standard deviations are used to recalculate a new mean for each pulse subsegment. Each pulse subsegment is detrended by subtracting each new mean from each pulse subsegment. Once each pulse subsegment is detrended, an ensemble (or column-wise) average of the subsegments (i.e., diastolic peak is averaged with diastolic peak, systolic valley is averaged with systolic valley, etc.) is calculated. This "ensemble" average may be accomplished by storing each detrended pulse in a row of a two-dimensional (2-D) array and taking the average of the data points in each column. FIG. 5 illustrates twelve individual pulse subsegments detrended and superimposed upon one another. FIG. 6 shows the modified average pulse as computed from the detrended pulse subsegments shown in FIG. 5.

Once the modified average pulse is determined for each candidate frequency, they are compared with each other to determine which one most closely matches a plethysmographic pulse. This determination is achieved by evaluating various known characteristics of a valid plethysmographic pulse. Such characteristics may take the form of rules relating to pulse timing, slopes, etc. that may be used to evaluate the validity of a candidate modified average pulse, see block 260 of FIG. 12. For example, one can observe the timing between systolic valley and diastolic peak to ensure that the time period falls within normal physiological limits. One can assume that the transition from diastole to systole is rapid and the transition from the systole back to diastole is relatively slow. Exemplar rules used to evaluate a candidate modified average pulse, (or a most recent pulse if the dispersion is sufficiently low) include, but are not limited to:

1. The time elapsed from diastolic peak to next diastolic peak, $t_1$, must obey physiological limits, for example, 240 milliseconds$<t_1<$2 seconds, or heart rate, HR, measured in beats per minute (bpm), must be within physiological limits, for example, 30 bpm$<$HR$<$250 bpm.

2. Similarly, the raw signal level at diastolic peak must be less than or equal to a maximum value which may be representative of a scaled voltage level. The maximum value may be selected from empirical measurements or other known characteristics of the measurement system.

3. The time elapsed between diastolic peak and systolic valley, $t_2$, must obey the following inequality: about 50 milliseconds$<t_2<$about 400 milliseconds.

4. The time elapsed between diastolic peak and systolic valley must be less than the time from systolic valley to the next diastolic peak. In other words, the slope of the data signal from diastolic peak to systolic valley is steeper than from systolic valley to the next diastolic peak. Or, the absolute value of the slope of the data signal from diastolic peak to systolic valley should greater than the absolute value of the slope of the data signal from systolic valley to the next diastolic peak.

5. The width of the candidate pulse cannot vary outside a given percentage of the average pulse width of each of the pulses within the data segment. For example the candidate pulse width must be within ±25% of the average pulse width for the pulses identified within the 10.24 seconds of data comprising the data segment.

6. The slope of the data signal from diastolic peak to systolic valley must be negative (descending) and the slope of the data signal from systolic valley to the next diastolic peak must be positive (ascending).

The above rules are exemplary only, and not intended to be limiting. Furthermore, the various rules selected to evaluate pulse shape may be assigned various weights to emphasize relative importance. The above rules may been assigned binary values depending on whether the rule is satisfied or not. Alternatively, the rules may be assigned weights depending on relative importance. In any case, the above rules may be applied to a candidate average pulse and are summed to obtain a quality number. The more rules that are satisfied, the higher the quality measure. The resulting quality measures for each candidate frequency may be statistically analyzed using trend analysis and a histogram to determine past performance at these frequencies. Such statistical analysis is within the knowledge of one of skill in the art, and thus, will not be further detailed herein.

The above processing is performed for all candidate frequencies, see block 280 of FIG. 12. The modified average pulse with the highest quality measure is selected, see block 290 of FIG. 12. The modified average pulse is then scaled to place each diastolic peak at the same signal level to allow the pulses to be appended to one another without discontinuity. Once the modified average pulse has been scaled it may be made available for further processing, for example, in a blood oxygen saturation calculation, see block 130 of FIG. 1.

Figure 7:
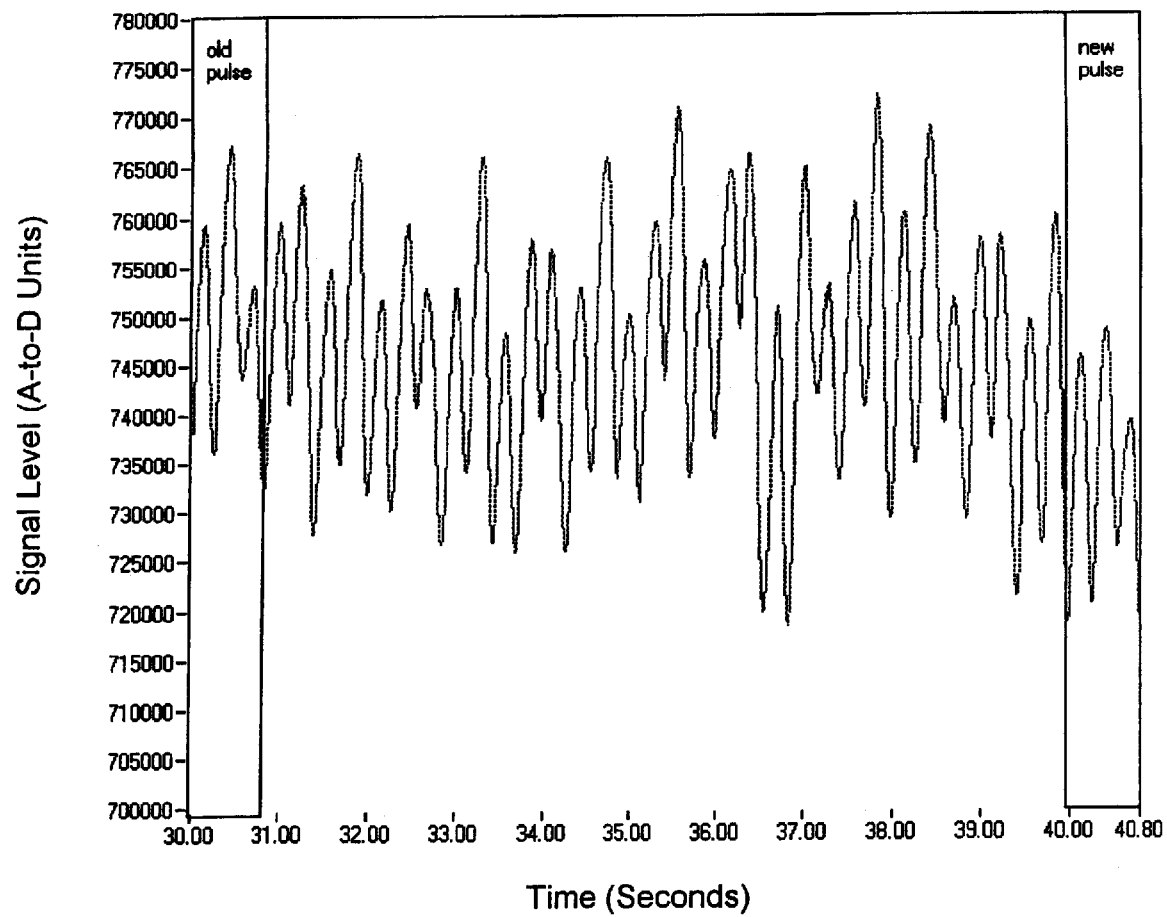
FIG. 7 illustrates the acquisition of a new pulse segment of raw IR data and the removal of the oldest segment of raw IR data in accordance with the invention.

The above methods may be integrated into apparatuses and/or systems for calculating blood oxygen saturation. In such pulse oximetry apparatuses and systems, the same signal processing as described above is performed on both a red and an IR data signal. The scaled and modified average pulses for red and IR signals may be pre-processed and then made available to an oxygen saturation algorithm for calculation of arterial oxygen saturation. The above methods may be repeated once another full heartbeat pulse of data is collected for both the red and IR signals, see block 140 of FIG. 1. The new pulse of data is added to the red and IR segments, respectively, and the oldest pulse of data is removed, FIG. 7 illustrates the acquisition of a new pulse segment of raw IR data and the removal of the oldest segment of raw IR data.

Figure 8:
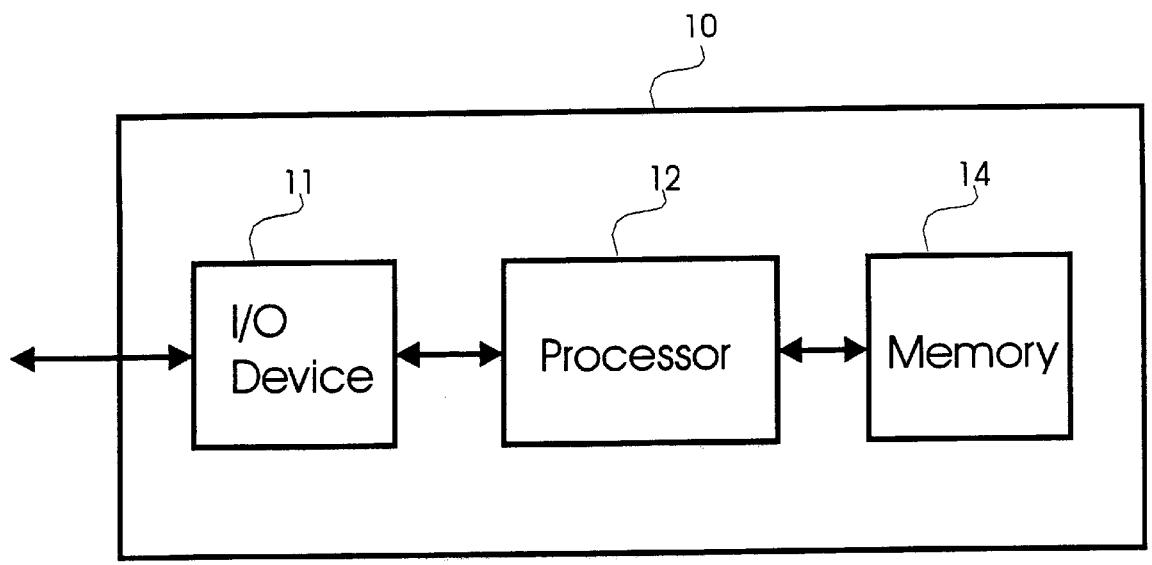
FIG. 8 is a block diagram of a motion artifact rejection circuit card configured to remove noise artifacts from signals representing bodily parameters in accordance with the invention.

Referring to FIG. 8, the apparatus embodiment of this invention is a motion artifact rejection circuit card 10 with an I/O device 11, a processor 12 and memory 14 for storing a computer programmed algorithm for motion artifact rejection as described in the above methods. Processor 12 may be a digital signal processor. I/O device 11 may be any circuitry that allows communication to and from external circuitry, for example, and not by way of limitation, bus interface circuitry. I/O device 11 may include a circuit card edge connector for plugging into a pulse oximetry monitor system. Memory 14 may be any solid state electronic memory suitable for storing digital data including, for example, computer code and measurement data.

Figure 9:
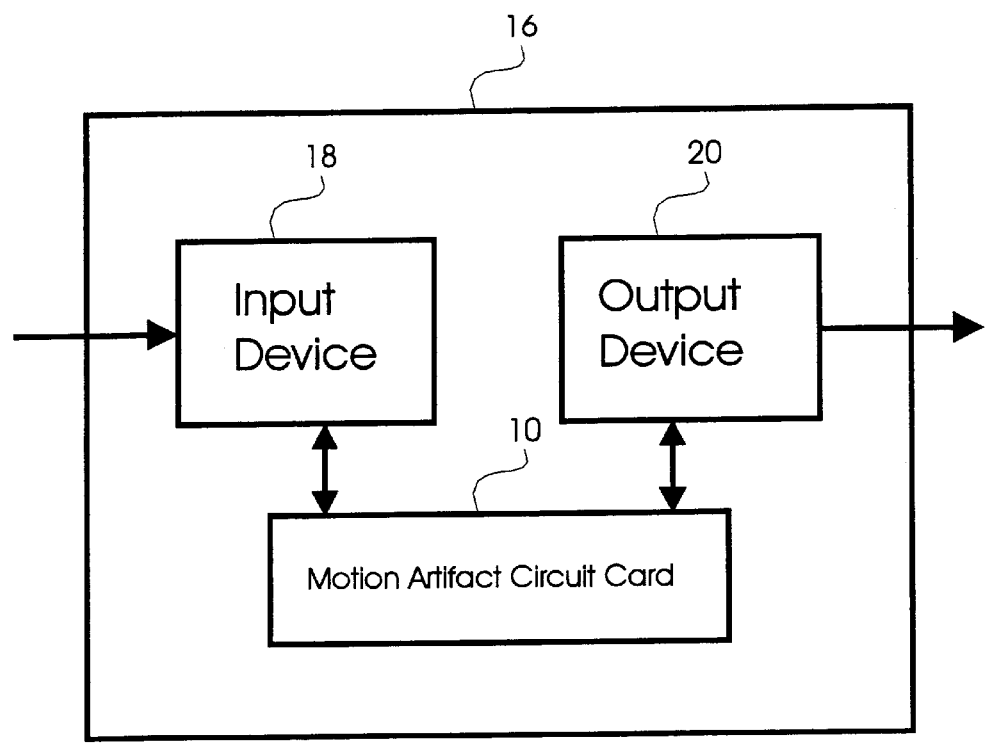
FIG. 9 is a block diagram of a pulse oximetry system including a motion artifact rejection circuit card capable of removing noise from pulse oximetry data in accordance with the invention.

Referring to FIG. 9, the motion artifact rejection circuit card 10 of FIG. 8 may be part of a complete pulse oximetry system 16 for eliminating motion-induced noise artifacts in electrical signals (as described in the method embodiments above) and calculating and displaying physiological parameters. The pulse oximetry system 16 also includes an input device 18 and an output device 20. Input device 18 may be a pulse oximeter sensor with red and IR LED light sources and a photodetector to convert transmitted or reflected light into an electrical signal. Output device 20 may be a display device such as a cathode ray tube device, liquid crystal display, active matrix display or any other suitable display device known to one of skill in the art. Alternatively, output device 20 may be a printer for producing a permanent or written record such as a laser printer, ink jet printer, thermal printer, dot matrix printer or any other suitable printer known to one of skill in the art. The pulse oximetry system 16 may be any pulse oximeter which uses the principles of operation as described above. A particular pulse oximeter suitable for use with the circuit card embodiment as described above is the Novametrix Medical Systems, Inc., Model 520A, Pulse Oximeter.

Figure 10:
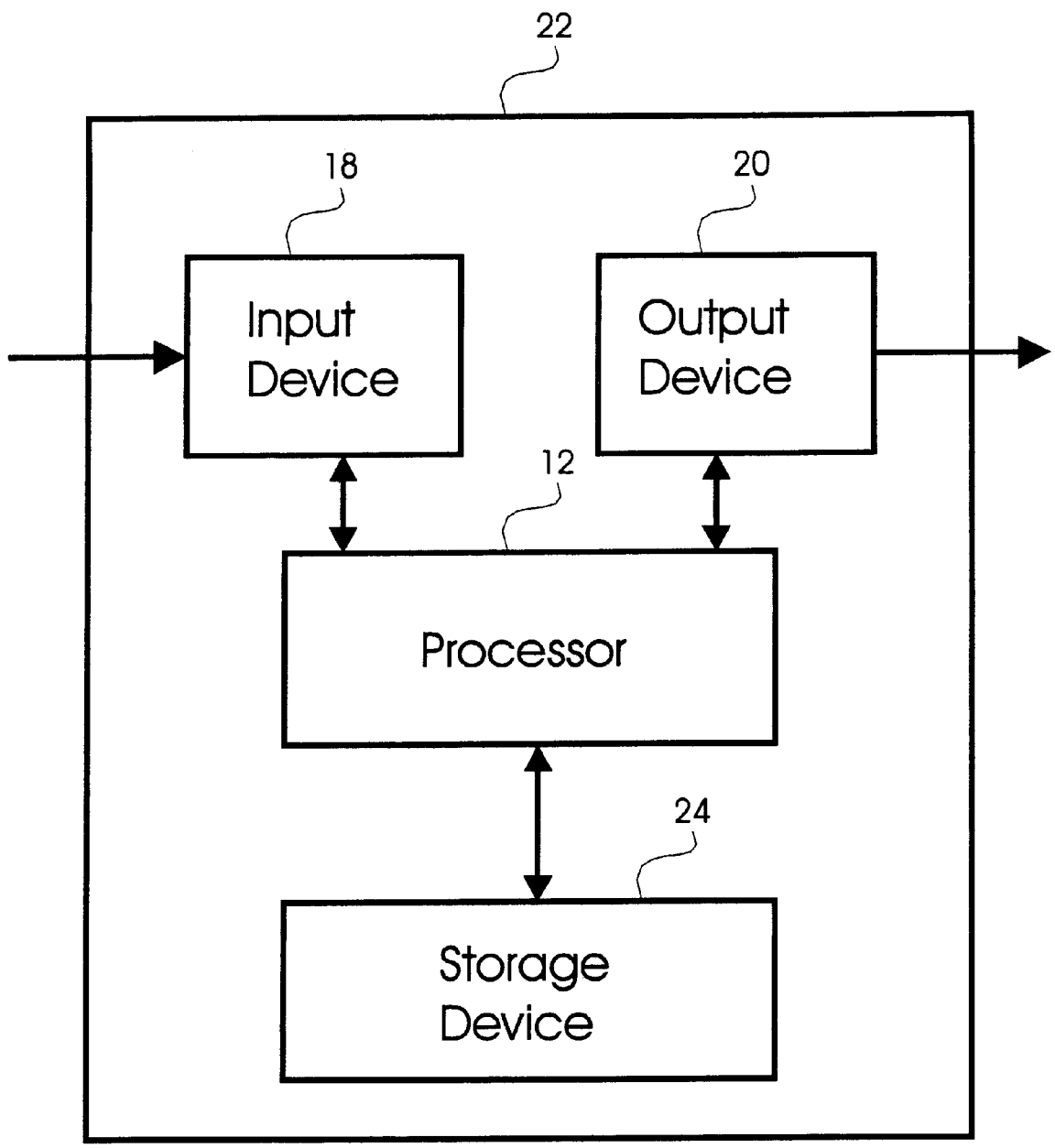
FIG. 10 is a block diagram of a pulse oximetry system including a processor device programmed to remove noise from pulse oximetry data in accordance with the invention.

Referring to FIG. 10, a block diagram of a pulse oximetry system 22 including a processor device 12, an input device 18, an output device 20 and a storage device 24, is shown. Input device 18 may be a pulse oximeter sensor with red and IR LED light sources and a photodetector to convert transmitted or reflected light into an electrical signal. Output device 20 may be a display device such as a cathode ray tube device, liquid crystal display, active matrix display or any other suitable display device known to one of skill in the art. Alternatively, output device 20 may be a printer for producing a permanent or written record such as a laser printer, ink jet printer, thermal printer, dot matrix printer or any other suitable printer known to one of skill in the art. Storage device 24 may be a disk drive, or any kind of solid state electronic memory device suitable for storing digital data including, for example, computer code and measurement data.

Although this invention has been described with reference to particular embodiments, the invention is not limited to these described embodiments. Rather, it should be understood that the embodiments described herein are merely exemplary and that a person skilled in the art may make many variations and modifications without departing from the spirit and scope of the invention. All such variations and modifications are intended to be included within the scope of the invention as defined in the appended claims.

What is claimed is:

1. A method of removing motion-induced noise artifacts from a single electrical signal representative of a pulse oximetry light signal, comprising:

receiving a segment of raw data spanning a plurality of heartbeats from said single electrical signal;

analyzing said segment of raw data for candidate frequencies, one of which said candidate frequencies may be representative of a valid plethysmographic pulse;

analyzing each of said candidate frequencies to determine a best frequency including narrow bandpass filtering said segment of raw data at each of said candidate frequencies;

outputting an average pulse signal computed from said segment of raw data and said best frequency; and repeating the above steps with a new segment of raw data.

2. The method of claim 1, wherein said analyzing said segment of raw data for candidate frequencies includes computing a power spectrum of said segment of raw data and identifying n candidate frequencies associated with the n largest amplitude peaks in power spectrum which are not harmonics of each other.

3. The method of claim 2, wherein n equals two.

4. The method of claim 3, further including comparing said two candidate frequencies with a previous known valid frequency and replacing the smaller amplitude candidate frequency with said previous known valid frequency if neither of said two candidate frequencies is within about ±0.1 Hertz of said previous known valid frequency.

5. The method of claim 2, further including filtering said segment of raw data to reduce spectral leakage prior to computing said power spectrum.

6. The method of claim 2, wherein said analyzing each of said candidate frequencies to determine a best frequency by selecting n candidate frequencies associated with the n largest amplitude peaks in power spectrum which are not harmonics of each other further comprises:

subsegmenting said bandpass filtered segment of raw data into individual heartbeat subsegments;

computing an average heartbeat pulse from said individual heartbeat subsegments;

evaluating said average heartbeat pulse against known plethysmographic pulse characteristics to obtain a quality measure for said average heartbeat pulse;

repeating the above steps for each of said n candidate frequencies; and selecting a candidate frequency and average heartbeat pulse with highest quality measure to be said best frequency.

7. The method of claim 6, wherein said bandpass filter is a finite impulse response (FIR) filter.

8. The method of claim 7, wherein the coefficients of said FIR filter are adjusted to place the center frequency of said FIR filter at said candidate frequency.

9. The method of claim 6, wherein said computing an average heartbeat pulse from said individual heartbeat subsegments comprises:

calculating an average for each individual heartbeat subsegment;

aligning corresponding individual heartbeat subsegment points from beginning to end for each of said individual heartbeat subsegments; and calculating a modified average pulse by eliminating all data points outside x standard deviations from said average for each individual heartbeat subsegment to obtain said average heartbeat pulse.

10. The method of claim 9, wherein x equals about two.

11. The method of claim 6, further comprising minimizing dispersion of saturation values, wherein said minimizing dispersion of saturation values includes adjusting the phase relationship of red and IR pulses and calculating a minimum dispersion of saturation values.

12. The method of claim 11, wherein adjusting the phase relationship of red and IR pulses includes calculating saturation values for a plurality of delays between said red and IR signals, wherein said plurality of delays are sequentially swept from about −20 ms to about +20 ms in 1 ms increments.

13. The method of claim 11, wherein minimizing dispersion of saturation values includes:

generating a histogram of saturation values with bin sizes of about y percent calculated with delays;

locating a peak bin and its immediately surrounding z bins and calculating a measure of dispersion based on the percentage of saturation values which fall within said peak bin and its immediately surrounding z bins; and selecting an optimum delay corresponding to measure of dispersion with highest percentage.

14. The method of claim 13, wherein y equals 0.25.

15. The method of claim 13, wherein z equals two.

16. A method of removing motion-induced noise artifacts from a measured pulse oximetry signal comprising:

acquiring a segment of pulse oximetry data from the measured pulse oximetry signal;

filtering said segment of pulse oximetry data;

performing frequency analysis on said filtered segment of pulse oximetry data to determine frequency components of said filtered segment of pulse oximetry data;

selecting a frequency component with a largest power as an initial candidate heart rate response;

subsegmenting said filtered segment of pulse oximetry data into a plurality of subsegments, wherein each subsegment represents an individual heartbeat;

averaging data values for each subsegment at identical points along said length of each subsegment to form an average subsegment;

determining whether said average subsegment represents a valid pulse oximetry signal;

outputting valid average subsegments;

updating said segment of pulse oximetry data;

measuring dispersion of saturation of latest pulse subsegment to determine whether said averaging step may be skipped; and repeating the above steps.

17. A method of removing motion-induced noise artifacts from measured pulse oximetry signals prior to calculating functional pulsatile blood oxygen concentration, $SpO_2$, comprising:

acquiring a red data segment spanning a plurality of heartbeats from oldest to newest;

frequency analyzing said red data segment for candidate red frequency components, one of which may be representative of a valid plethysmographic pulse;

analyzing each of said candidate red frequency components to determine a best red frequency component including narrow bandpass filtering said segment of red data at each of said candidate red frequency components;

outputting an average red pulse signal computed from said red data segment and said best red frequency component;

repeating the above steps with a new red data segment; and substantially simultaneously performing the above steps with respect to an infrared data segment.

18. A method of removing motion-induced noise artifacts from a single electrical signal representative of a pulse oximetry light signal comprising:

(a) acquiring a segment of raw data spanning a plurality of heartbeats from said single electrical signal;

(b) frequency analyzing said segment of raw data to determine two candidate frequencies with greatest amplitude, $F_1$ and $F_2$, which are not harmonics of each other;

(c) removing $F_2$ from said segment of raw data to obtain $F_2$ filtered data;

(d) subsegmenting said $F_2$ filtered data into a plurality of subsegments each containing a single heartbeat pulse;

(e) calculating a first average pulse signal based on averaging said plurality of $F_2$ filtered subsegments;

(f) removing $F_1$ from said segment of raw data to obtain $F_1$ filtered data;

(g) subsegmenting said $F_1$ filtered data into a plurality of subsegments each containing a single heartbeat pulse;

(h) calculating a second average pulse signal based on averaging said plurality of $F_1$ filtered subsegments;

(i) determining which of said first average pulse signal and said second average pulse signal represents a valid plethysmographic pulse;

(j) outputting said first average pulse signal or said second average pulse signal which represents a valid plethysmographic pulse; and (k) repeating steps (b) through (j) with a new segment of raw data.

19. The method of claim 18, wherein after step (b), frequencies $F_1$ and $F_2$ are compared with a valid frequency, $F_0$, from a previous signal processing cycle and $F_0$ is substituted for $F_2$ if neither $F_1$ or $F_2$ are ±0.1 Hertz of $F_0$.

20. The method of claim 18, wherein removing $F_2$ from said segment of raw data is accomplished by filtering said segment of raw data with a bandstop filter of a width about 0.5 Hertz centered at $F_2$.

21. A method of removing motion-induced noise artifacts from a measured pulse oximetry signal comprising:

acquiring a segment of pulse oximetry data from the measured pulse oximetry signal;

filtering said segment of pulse oximetry data;

performing frequency analysis on said filtered segment of pulse oximetry data to determine frequency components of said filtered segment of pulse oximetry data;

selecting a frequency component with a largest power as an initial candidate heart rate response;

narrow bandpass filtering at said selected frequency component;

subsegmenting said filtered segment of pulse oximetry data into a plurality of subsegments, wherein each subsegment represents an individual heartbeat;

averaging data values for each subsegment at identical points along said length of each subsegment to form an average subsegment;

determining whether said average subsegment represents a valid pulse oximetry signal;

selecting a next largest power frequency component, if one exists, and repeating said narrow bandpass filtering step, said subsegmenting step, said averaging step and said determining step;

outputting valid average subsegments;

updating said segment of pulse oximetry data; and repeating the above steps.

22. The method of claim 21, further comprising measuring dispersion of saturation of latest pulse subsegment to determine whether said averaging step may be skipped.

23. The method of claim 21, further comprising minimizing dispersion of saturation values prior to said outputting valid average subsegments.

24. A circuit card for use in a pulse oximetry system to remove motion-induced noise artifacts from a measured pulse oximetry signal, said circuit card comprising:

a circuit board for mounting electronic circuitry and interfacing with the pulse oximetry system;

a processor mounted on said circuit board for processing at least one input signal according to instructions; and memory for storing a computer program, wherein said memory is operably coupled to said processor, and wherein said computer program includes instructions for implementing a method of removing motion artifacts from said measured pulse oximetry signal, said method comprising:

receiving a segment of raw data spanning a plurality of heartbeats from said measured pulse oximetry signal;

analyzing said segment of raw data for candidate frequencies one of which said candidate frequencies may be representative of a valid plethysmographic pulse including narrow bandpass filtering said segment of raw data at each of said candidate frequencies;

analyzing each of said candidate frequencies to determine a best frequency based on highest quality measure;

outputting an average pulse signal computed from said segment of raw data and said best frequency; and repeating the above steps with a new segment of raw data.

25. The circuit card of claim 24, wherein said processor is a digital signal processor.

26. A pulse oximetry system for removing motion-induced noise artifacts from measured pulse oximetry signals comprising an input device, an output device, and a motion artifact circuit card, wherein said motion artifact circuit card comprises:

a circuit board configured for coupling to said pulse oximetry system and communicating with other electronics within said pulse oximetry system;

a processor mounted on said circuit board for processing at least one input signal according to instructions; and memory operably coupled to said processor for storing a computer program, wherein said computer program includes instructions for implementing a method of removing motion artifacts from said measured pulse oximetry signal, wherein said method comprises:

receiving a segment of raw data spanning a plurality of heartbeats from said measured pulse oximetry signal;

analyzing said segment of raw data for candidate frequencies one of which said candidate frequencies may be representative of a valid plethysmographic pulse including narrow bandpass filtering said segment of raw data at each of said candidate frequencies;

analyzing each of said candidate frequencies to determine a best frequency based on highest quality measure;

outputting an average pulse signal computed from said segment of raw data and said best frequency; and repeating the above steps with a new segment of raw data.

27. The pulse oximetry system of claim 26, wherein said processor is a digital signal processor.

28. A pulse oximetry system for removing motion-induced noise artifacts from measured pulse oximetry signals comprising an input device, an output device, and a motion artifact circuitry, wherein said motion artifact circuitry includes:

a processor for processing at least one input signal according to instructions; and memory operably coupled to said processor for storing a computer program, wherein said computer program includes instructions for implementing a method of removing motion artifacts from said measured pulse oximetry signal, wherein said method comprises:

receiving a segment of raw data spanning a plurality of heartbeats from said signal;

analyzing said segment of raw data for candidate frequencies one of which said candidate frequencies may be representative of a valid plethysmographic pulse including narrow bandpass filtering said segment of raw data at each of said candidate frequencies;

analyzing each of said candidate frequencies to determine a best frequency based on highest quality measure;

outputting an average pulse signal computed from said segment of raw data and said best frequency; and repeating the above steps with a new segment of raw data.

29. The pulse oximetry system of claim 28, wherein said processor is a digital signal processor.

30. A method of removing motion-induced noise artifacts from a single electrical signal representative of a pulse oximetry light signal, comprising:

receiving a segment of raw data spanning a plurality of heartbeats from said single electrical signal;

analyzing said segment of raw data for candidate frequencies, one of which said candidate frequencies may be representative of a valid plethysmographic pulse, said analyzing including computing a power spectrum of said segment of raw data and identifying n candidate frequencies associated with n largest amplitude peaks in power spectrum which are not harmonics of each other, further comprising:

bandpass filtering said segment of raw data;

subsegmenting said bandpass filtered segment of raw data into heartbeat subsegments, comprising:

beginning each heartbeat subsegment at one quarter pulse width before a diastolic peak; and ending each heartbeat subsegment at one quarter pulse width after an immediately following diastolic peak, wherein each heartbeat subsegment overlaps with both a preceding heartbeat subsegment and a succeeding heartbeat subsegment, and each plethysmographic pulse is centered within each heartbeat subsegment;

computing an average heartbeat pulse from said heartbeat subsegments;

evaluating said average heartbeat pulse against known plethysmographic pulse characteristics to obtain a quality measure for said average heartbeat pulse;

repeating the above steps for each of said n candidate frequencies; and selecting a candidate frequency and average heartbeat pulse with highest quality measure to be said best frequency;

analyzing each of said candidate frequencies to determine a best frequency;

outputting an average pulse signal computed from said segment of raw data and said best frequency; and repeating the above steps with a new segment of raw data.

31. A method of removing motion-induced noise artifacts from a single electrical signal representative of a pulse oximetry light signal, comprising:

receiving a segment of raw data spanning a plurality of heartbeats from said single electrical signal;

analyzing said segment of raw data for candidate frequencies, one of which said candidate frequencies may be representative of a valid plethysmographic pulse, said analyzing including computing a power spectrum of said segment of raw data and identifying n candidate frequencies associated with n largest amplitude peaks in power spectrum which are not harmonics of each other, further comprising:

bandpass filtering said segment of raw data;

subsegmenting said bandpass filtered segment of raw data into individual heartbeat subsegments;

computing an average heartbeat pulse from said individual heartbeat subsegments;

evaluating said average heartbeat pulse against known plethysmographic pulse characteristics to obtain a quality measure for said average heartbeat pulse;

repeating the above steps for each of said n candidate frequencies;

selecting a candidate frequency and average heartbeat pulse with highest quality measure to be said best frequency; and minimizing dispersion of saturation values including adjusting the phase relationship of red and IR pulses including calculating saturation values for a plurality of delays between said red and IR signals, wherein said plurality of delays are sequentially swept from about −20 ms to about +20 ms in 1 ms increments and calculating a minimum dispersion of saturation values;

analyzing each of said candidate frequencies to determine a best frequency;

outputting an average pulse signal computed from said segment of raw data and said best frequency; and repeating the above steps with a new segment of raw data.

32. A method of removing motion-induced noise artifacts from a single electrical signal representative of a pulse oximetry light signal, comprising:

receiving a segment of raw data spanning a plurality of heartbeats from said single electrical signal;

analyzing said segment of raw data for candidate frequencies, one of which said candidate frequencies may be representative of a valid plethysmographic pulse, said analyzing including computing a power spectrum of said segment of raw data and identifying n candidate frequencies associated with n largest amplitude peaks in power spectrum which are not harmonics of each other, further comprising:

bandpass filtering said segment of raw data;

subsegmenting said bandpass filtered segment of raw data into individual heartbeat subsegments;

computing an average heartbeat pulse from said individual heartbeat subsegments;

evaluating said average heartbeat pulse against known plethysmographic pulse characteristics to obtain a quality measure for said average heartbeat pulse;

repeating the above steps for each of said n candidate frequencies;

selecting a candidate frequency and average heartbeat pulse with highest quality measure to be said best frequency; and minimizing dispersion of saturation values including adjusting the phase relationship of red and IR pulses and calculating a minimum dispersion of saturation values including:

generating a histogram of saturation values with bin sizes of about y percent calculated with delays;

locating a peak bin and its immediately surrounding z bins and calculating a measure of dispersion based on the percentage of saturation values which fall within said peak bin and it immediately surrounding z bins; and selecting an optimum delay corresponding to measure of dispersion with highest percentage;

analyzing each of said candidate frequencies to determine a best frequency;

outputting an average pulse signal computed from said segment of raw data and said best frequency; and repeating the above steps with a new segment of raw data.

33. The method of claim 32, wherein y equals 0.25.

34. The method of claim 32, wherein z equals two.

* * * * *

UNITED STATES PATENT AND TRADEMARK OFFICE
CERTIFICATE OF CORRECTION

PATENT NO. : 6,393,311 B1
DATED : May 21, 2002
INVENTOR(S) : Reuben W. Edgar, Jr. et al.

It is certified that error appears in the above-identified patent and that said Letters Patent is hereby corrected as shown below:

Column 1,
Line 24, change the comma after "processes" to a period

Column 4,
Line 17, change "η" to -- β --
Line 47, change "oximetty" to -- oximetry --
Line 50, change "K nan" to -- Kalman --

Column 11,
Line 1, before "greater" insert -- be --

Column 13,
Line 51, before "phase" change "the" to -- a --
Line 65, at the end of the line change "the" to -- a --

Column 17
Line 5, after "said" and before "signal" insert -- measured pulse oximetry --
Line 54, before "best" change "said" to -- a --
Line 57, before "best" change "a" to -- said --

Column 18,
Line 21, before "phase" change "the" to -- a --

Column 19,
Line 2, change "it" to -- its --

Signed and Sealed this

Sixth Day of January, 2004

JAMES E. ROGAN
*Director of the United States Patent and Trademark Office*